United States Patent
Deur-Bert et al.

(10) Patent No.: US 9,776,938 B2
(45) Date of Patent: Oct. 3, 2017

(54) PLANT FOR PRODUCING 2,3,3,3-TETRAFLUOROPROPENE

(71) Applicant: Arkema France, Colombes (FR)

(72) Inventors: Dominique Deur-Bert, Charly (FR); Bertrand Collier, Saint-Genis-Laval (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/139,662

(22) Filed: Apr. 27, 2016

(65) Prior Publication Data

US 2016/0237009 A1    Aug. 18, 2016

Related U.S. Application Data

(62) Division of application No. 14/376,190, filed as application No. PCT/FR2013/050064 on Jan. 11, 2013, now Pat. No. 9,346,723.

(30) Foreign Application Priority Data

Feb. 3, 2012    (FR) ...................... 12 51021

(51) Int. Cl.
*C07C 17/00* (2006.01)
*C07C 17/093* (2006.01)
(Continued)

(52) U.S. Cl.
CPC ............ *C07C 17/20* (2013.01); *C07C 17/206* (2013.01); *C07C 17/25* (2013.01); *C07C 17/383* (2013.01);
(Continued)

(58) Field of Classification Search
CPC ....... C07C 17/00; C07C 17/093; C07C 17/20; C07C 17/202; C07C 17/206; C07C 17/25;
(Continued)

(56) References Cited

U.S. PATENT DOCUMENTS

2009/0270659 A1    10/2009    Collier et al.
2011/0218369 A1    9/2011    Elsheikh et al.

FOREIGN PATENT DOCUMENTS

WO    WO2009/015317    1/2009
WO    WO 2009/105512 A1 *    8/2009
(Continued)

OTHER PUBLICATIONS

International Search Report for PCT/FR2013/050064 dated Jun. 19, 2013.

*Primary Examiner* — Natasha Young
(74) *Attorney, Agent, or Firm* — Brinks Gilson & Lione

(57) ABSTRACT

The invention concerns a method for producing 2,3,3,3-tetrafluoropropene comprising: a fluoridation reaction of a halopropane and/or halopropene into 2,3,3,3-tetrafluoropropene by means of hydrogen fluoride; the recovery of a gas stream resulting from the reaction; the cooling and partial condensation of the gas stream resulting from the reaction into a partially condensed stream; the separation of the partially condensed stream into a gas fraction and a liquid fraction; the compression of the gas fraction into a compressed gas fraction; the compression of the liquid fraction into a compressed liquid fraction; the distillation of the compressed gas fraction and compressed liquid fraction in order to provide a stream of 2,3,3,3-tetrafluoropropene, a stream of hydrochloric acid, and a stream of unreacted hydrogen fluoride. The invention also concerns an installation suitable for implementing said method.

8 Claims, 1 Drawing Sheet

(51) Int. Cl.
  *C07C 17/20* (2006.01)
  *C07C 17/25* (2006.01)
  *C07C 17/38* (2006.01)
  *C07C 17/383* (2006.01)
  *C07C 21/00* (2006.01)
  *C07C 21/02* (2006.01)
  *C07C 21/18* (2006.01)
  *F25J 1/00* (2006.01)
  *F25J 3/04* (2006.01)

(52) U.S. Cl.
  CPC ......... *F25J 1/0022* (2013.01); *F25J 3/04412* (2013.01); *C07C 17/38* (2013.01)

(58) Field of Classification Search
  CPC ....... C07C 17/38; C07C 17/383; C07C 21/00; C07C 21/02; C07C 21/18; F25J 1/00; F25J 1/0002; F25J 1/0022; F25J 3/00; F25J 3/02; F25J 3/04; F25J 3/04406; F25J 3/04412
  See application file for complete search history.

(56) References Cited

FOREIGN PATENT DOCUMENTS

| WO | WO2009/158321 | 12/2009 |
| WO | WO 2010/050373 A2 * | 5/2010 |
| WO | WO 2010/059493 A1 * | 5/2010 |
| WO | WO 2010/123154 A2 * | 10/2010 |
| WO | WO2011/077192 | 6/2011 |

\* cited by examiner

PLANT FOR PRODUCING 2,3,3,3-TETRAFLUOROPROPENE

CROSS-REFERENCE TO RELATED APPLICATIONS

This application is a Divisional of U.S. patent application Ser. No. 14/376,190, now U.S. Pat. No. 9,346,723, filed Dec. 3, 2014, now allowed; which is a National Stage application of International Application No. PCT/FR2013/050064, now WO/2013/114015, filed Jan. 11, 2013. This application also claims priority under 35 U.S.C. §119 to French Application No. 1251021 filed Feb. 3, 2012.

FIELD OF THE INVENTION

The present invention pertains to a method for producing 2,3,3,3-tetrafluoropropene (HFO-1234yf), in particular from 1,1,1,2,3-pentachloropropane (HCC-240db) and/or from 1,1,2,2,3-pentachloropropane (HCC-240aa), and also to a plant suitable for the implementation of said method.

TECHNICAL BACKGROUND

The Montreal protocol for the protection of the ozone layer led to the abandoning of the use of chlorofluorocarbons (CFCs). Compounds less harmful for the ozone layer, such as hydrofluorocarbons (HFCs), therefore replaced the chlorofluorocarbons. These compounds, however, are relatively substantial contributors to the greenhouse effect. There is therefore a need for effective compounds combining a low ODP (ozone-depleting potential) with a low GWP (global warming potential). Hydrofluoroolefins (HFOs) have been identified as desirable alternatives, by virtue of their low ODP and GWP values.

The compound 2,3,3,3-tetrafluoropropene (HFO-1234yf) is of particular interest in this regard.

A number of documents relate to processes for preparing fluorinated olefins from pentachloropropane.

For example, document US 2009/0240090 describes the reaction of 1,1,1,2,3-pentachloropropane (HCC-240db) to give 2-chloro-3,3,3-trifluoropropene (HCFO-1233xf) in the absence of oxygen. The resulting HCFO-1233xf is converted to 2-chloro-1,1,1,2-tetrafluoropropane (HCFC-244bb).

Document WO 2009/015317 describes the reaction of a chlorinated compound such as 1,1,2,3-tetrachloropropene (HCO-1230xa), HCC-240db, or 2,3,3,3-tetrachloropropene (HCO-1230xf) with hydrogen fluoride (HF), in the gas phase. This process can be used to obtain HCFO-1233xf.

Document WO 2005/108334 describes the reaction of HCC-240db with HF to give 2-chloro-1,1,1,3-tetrafluoropropane (HCFC-244db), which is then dehydrochlorinated to give 1,3,3,3-tetrafluoropropene (HFO-1234ze).

Document WO 2010/123148 describes the fluorination of HCC-240db to HCFO-1233xf in the absence of catalyst.

Patent application PCT/IB2010/003028, filed by the applicant, describes the catalytic gas-phase fluorination of HCC-240db or of 1,1,2,2,3-pentachloropropane (HCC-240aa) to HFO-1234yf.

In the context of this process, however, it is necessary to separate the compounds obtained from the reaction step, namely the desired HFO-1234yf product, other fluorinated compounds formed during the reaction, hydrochloric acid (HCl), which is also formed during the reaction, the unreacted reactants (particularly HF), degradation products, or inert compounds.

In order to do this, it is possible to use an assembly of distillation columns that produces a stream of HFO-1234yf, an HCl stream, and a stream intended for recycling to the reaction. But the boiling points of HCl and of HFO-1234yf are relatively low (−85° C. for HCl at atmospheric pressure and −29.1° C. for HFO-1234yf at atmospheric pressure). Condensing the gases at the top of the distillation columns therefore requires a high operating pressure, so that the temperature needed at the top of the column is not too low, and therefore so that the process is compatible with the use of standard cold units.

Typically, the operating pressure required for distillative separation is greater than 5 bar, or even greater than 7 bar. The reactor must therefore be operated at an even higher pressure. This presents problems in so far as, in certain configurations, it is desirable to operate at a relatively low pressure in the reactor.

If the fluorination reaction is carried out at a lower pressure, the gases obtained from the reaction have to be compressed before distillation. That, however, implies an excessive compressor size, owing to the substantial excess of HF used in the fluorination reaction. This therefore represents a technology which is very complex to employ.

Consequently there is a genuine need to develop a method for producing HFO-1234yf wherein the fluorination reaction can be implemented at a moderate pressure.

SUMMARY OF THE INVENTION

The invention pertains firstly to a method for producing 2,3,3,3-tetrafluoropropene, comprising:
  reactively fluorinating a halopropane and/or halopropene to 2,3,3,3-tetrafluoropropene using hydrogen fluoride;
  recovering a gaseous stream obtained from the reaction;
  cooling and partially condensing the gaseous stream obtained from the reaction, to give a partially condensed stream;
  separating the partially condensed stream into a gaseous fraction and a liquid fraction;
  compressing the gaseous fraction to give a compressed gaseous fraction;
  compressing the liquid fraction to give a compressed liquid fraction;
  distilling the compressed gaseous fraction and the compressed liquid fraction to give a 2,3,3,3-tetrafluoropropene stream, a hydrochloric acid stream, and a stream of unreacted hydrogen fluoride.

In one embodiment the stream of unreacted hydrogen fluoride further comprises organic compounds which are intermediates from the fluorination reaction, and/or organic compounds obtained from secondary reactions.

In one embodiment the stream of unreacted hydrogen fluoride is recycled to the fluorination reaction.

In one embodiment the fluorination reaction is a gas-phase catalytic fluorination reaction.

In one embodiment the fluorination reaction is carried out at a pressure lower than that of the distillation of the compressed gaseous fraction and of the compressed liquid fraction.

In one embodiment the fluorination reaction is carried out at a pressure of from 0.1 to 10 bar abs, and preferably from 0.3 to 8 bar abs; and/or the distillation is carried out at a pressure of from 5 to 40 bar abs, and more preferably from 7 to 25 bar abs.

In one embodiment the gaseous fraction represents from 25% to 60% of the partially condensed stream, and the liquid fraction represents from 40% to 75% of the partially condensed stream, in proportions by mass.

In one embodiment the distillation step comprises:
a first distillation of the compressed gaseous fraction and of the compressed liquid fraction;
the recovery of the stream of unreacted hydrogen fluoride at the end of the first distillation;
the recovery of an intermediate stream at the end of the first distillation;
a second distillation of the intermediate stream;
the recovery of the hydrochloric acid stream at the end of the second distillation; and
the recovery of the 2,3,3,3-tetrafluoropropene stream at the end of the second distillation.

In an alternative embodiment the distillation step comprises:
a first distillation of the compressed gaseous fraction and of the compressed liquid fraction;
the recovery of the hydrochloric acid stream at the end of the first distillation;
the recovery of an intermediate stream at the end of the first distillation;
a second distillation of the intermediate stream;
the recovery of the 2,3,3,3-tetrafluoropropene stream at the end of the second distillation; and
the recovery of the stream of unreacted hydrogen fluoride at the end of the second distillation.

In one embodiment the compressed gaseous fraction and the compressed liquid fraction are introduced at different sites of a distillation column.

In one embodiment the 2,3,3,3-tetrafluoropropene stream undergoes one or more further purification steps, preferably selected from washing, extraction, decanting, and distillation.

In one embodiment the halopropane and/or halopropene is a chloropropane and/or chloropropene, and is preferably selected from 1,1,1,2,3-pentachloropropane, 1,1,2,2,3-pentachloropropane, 1,1,2,3-tetrachloropropene, 2,3,3,3-tetrachloropropene, 1,1,1-trifluoro-2-chloropropene, and 1,1,1-trifluoro-2,3-dichloropropane, and mixtures thereof.

The invention further pertains to a plant for producing 2,3,3,3-tetrafluoropropene, comprising:
at least one fluorination reactor supplied with halopropane and/or halopropene and with hydrogen fluoride;
a line for reaction gases, which is connected at the outlet of the fluorination reactor;
cooling and partial condensation means, which are supplied by the line for reaction gases;
a line for transporting partially condensed stream, which is connected at the outlet of the cooling and partial condensation means;
a separating flask supplied by the line for transporting partially condensed stream;
a line for withdrawing gaseous fraction and a line for withdrawing liquid fraction, which are connected at the outlet of the separating flask;
a compressor which is supplied by the line for withdrawing gaseous fraction;
a line for supplying compressed gaseous fraction, which is connected at the outlet of the compressor;
a pump which is supplied by the line for withdrawing liquid fraction;
a line for supplying compressed liquid fraction, which is connected at the outlet of the pump;
distillation means which are supplied by the line for supplying compressed gaseous fraction and by the line for supplying compressed liquid fraction;
a line for withdrawing 2,3,3,3-tetrafluoropropene, a line for withdrawing hydrochloric acid, and a line for withdrawing unreacted hydrogen fluoride, which are connected at the outlet of the distillation means.

In one embodiment the line for withdrawing unreacted hydrogen fluoride supplies the fluorination reactor In one embodiment the plant comprises heating means on the line for withdrawing gaseous fraction.

In one embodiment the distillation means comprise a first distillation column and a second distillation column, the line for supplying compressed gaseous fraction and the line for supplying compressed liquid fraction supplying the first distillation column.

In one embodiment:
the line for withdrawing unreacted hydrogen fluoride is connected at the bottom of the first distillation column;
a line for withdrawing intermediate stream is connected at the top of the first distillation column and supplies the second distillation column;
the line for withdrawing hydrochloric acid is connected at the top of the second distillation column; and
the line for withdrawing 2,3,3,3-tetrafluoropropene is connected at the bottom of the second distillation column.

In an alternative embodiment:
the line for withdrawing hydrochloric acid is connected at the top of the first distillation column;
a line for withdrawing intermediate stream is connected at the bottom of the first distillation column and supplies the second distillation column;
the line for withdrawing 2,3,3,3-tetrafluoropropene is connected at the top of the second distillation column; and
the line for withdrawing unreacted hydrogen fluoride is connected at the bottom of the second distillation column.

In one embodiment the line for supplying compressed gaseous fraction and the line for supplying compressed liquid fraction supply the first distillation column at different stages of said column.

In one embodiment the line for withdrawing 2,3,3,3-tetrafluoropropene supplies further purification means, preferably selected from washing, extraction, decanting, and distillation means.

The present invention allows the drawbacks in the prior art to be overcome. It provides more particularly a method for producing HFO-1234yf wherein the fluorination reaction can be implemented at a moderate pressure, and simply and economically, and in particular with no need to employ a compressor capable of compressing an excessive gas flow rate.

This is achieved through the provision of cooling and partial condensation of the gases obtained from the reaction step, followed by separation of these products into a liquid fraction and a gaseous fraction. In this way, only part of the gases obtained from the reaction (gaseous fraction) must be compressed in a compressor, while the liquid fraction (condensed gases) can be taken up by a pump, which is simpler to implement than a compressor.

Moreover, the gaseous fraction advantageously includes a low level of HF, the HF being located primarily in the liquid fraction. This simplifies the design of the compressor, particularly in terms of choice of materials, since this compressor is not required to be in contact with a large quantity of HF.

The invention therefore allows the fluorination reaction and the separation of the products obtained from the reaction to be operated at optimum, independent pressures.

In one particularly advantageous embodiment, the invention provides for the injection of the liquid fraction and of the gaseous fraction at different stages of a separating column, and this allows the design of the separating column to be optimized in terms of number of theoretical plates and of reflux ratio to be implemented. The size of the column and the heating power required for the condenser and the reboiler of the column can therefore be minimized, as well as the size of the cold unit associated with the condenser.

DESCRIPTION OF EMBODIMENTS OF THE INVENTION

The invention is now described in more detail, without limitation, in the description below.

Fluorination Reaction

Figure 1:
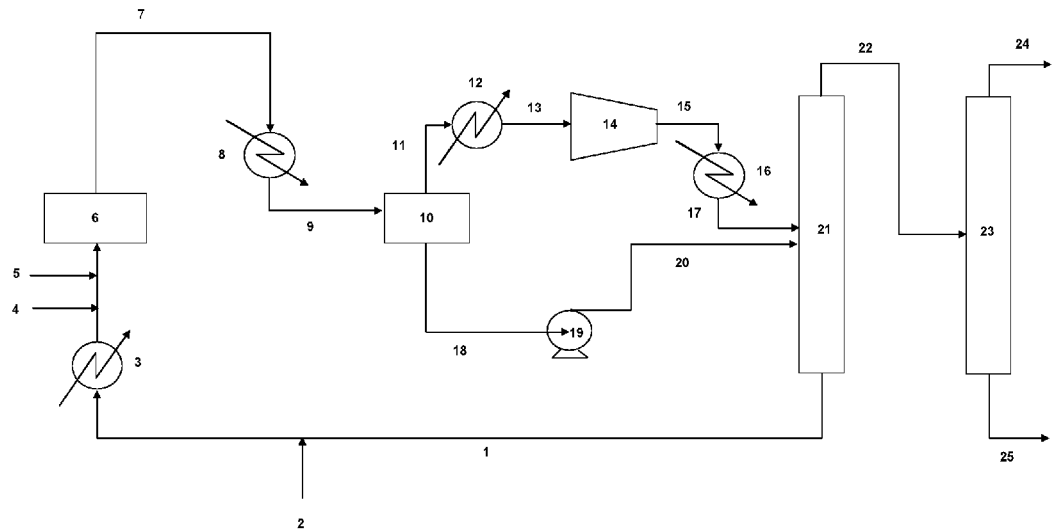
FIG. 1 represents schematically a plant in accordance with a first embodiment of the invention.

In a first embodiment, and with reference to FIG. 1, a plant according to the invention generally comprises a fluorination reactor 6. It is also possible to utilize two or more than two reactors arranged in series. This fluorination reactor is supplied with halopropane and/or halopropene by a hydrohalocarbon supply line 4, and with HF by an HF supply line 2.

For halopropane or halopropene, it is possible in particular to use any chlorofluoropropane and/or chlorofluoropropene, or, in a preferred embodiment, any chloropropane and/or chloropropene.

For example, the halopropanes of formula $CX_3CHClCH_2X$ or of formula $CHX_2CClXCH_2X$, the halopropenes of formula $CX_3CCl=CH_2$ or of formula $CX_2=CClCH_2X$, with each X independently representing F or Cl, may be suitable.

Preferred halopropanes and halopropenes are HCC-240db, HCC-240aa, HCO-1230xa, and HCO-1230xf, or else HCFO-1233xf and HCFC-243db (2,3-dichloro-1,1,1-trifluoropropane). Mixtures of these compounds are also possible.

The remainder of the description is given in relation to HCC-240db, on the understanding that the other halopropanes and/or halopropenes may be utilized analogously.

HCC-240db is converted to HFO-1234yf by reaction with HF in the fluorination reactor 6. The amount of HFO-1234yf in the stream obtained from the reaction is preferably at least 0.5 mol %, in particular at least 1 mol %, and more preferably at least 2 mol % or at least 3 mol %.

In addition to HCl, other compounds are formed during the reaction—for example, HCFO-1233xf and HFC-245cb (1,1,1,2,2-pentafluoropropane) in the case of a reaction starting from HCC-240db.

The fluorination reactor 6 is a catalytic reactor containing a catalyst.

The catalyst is, for example, based on a metal comprising a transition metal oxide or a derivative or a halide or an oxyhalide of such a metal. Examples of catalysts are $FeCl_3$, chromium oxyfluoride, chromium oxides (optionally subjected to fluorinating treatments), chromium fluorides, and mixtures thereof. Other possible catalysts are catalysts with a carbon support which are based on antimony and on aluminum ($AlF_3$, $Al_2O_3$, aluminum oxyfluoride, aluminum fluoride). Generally speaking, catalysts which may be used are chromium oxyfluoride, aluminum fluoride and oxyfluoride, and supported or unsupported catalysts containing a metal such as Cr, Ni, Zn, Ti, V, Zr, Mo, Ge, Sn, Pb, Mg. Reference may also be made to documents WO 2007/079431 at page 7 lines 1-5 and 28-32, EP 0939071 in paragraph [0022], WO 2008/054781 at page 9 line 22-page 10 line 34, and WO 2008/040969 in claim 1, all of which are incorporated here by reference.

Before use, the catalyst is subjected to activation, typically with air, oxygen, or chlorine and/or with HF, under appropriate conditions.

In one preferred embodiment, a mixed catalyst is used which comprises both chromium and nickel. The molar Cr:Ni ratio, in terms of metallic elements, is generally from 0.5 to 5, from 0.7 to 2 for example, approximately 1, for example. The catalyst may comprise, by mass, from 0.5% to 20% of chromium and from 0.5% to 20% of nickel, preferably from 2% to 10% of each metal.

The metal may be present in metallic form or in the form of a derivative, especially oxide, halide, or oxyhalide. These derivatives, especially halides and oxide halides, are obtained by activation of the catalytic metal. While the activation of the metal is not necessary, it is preferred.

The support is preferably prepared from aluminum, as for example alumina, activated alumina, or aluminum derivatives. These derivatives comprise aluminum halides and aluminum oxide halides, examples being those described in document U.S. Pat. No. 4,902,838, or those obtained by activation.

The catalyst may comprise chromium and nickel in activated or unactivated form, on a support which has or has not been subjected to activation.

Reference may be made to document WO 2009/118628, and in particular to the description of the catalyst from page 4 line 30 to page 7 line 16, which is incorporated here by reference.

According to another particularly preferred embodiment, the catalyst may also be Cr of high specific surface area, preferably unsupported. The catalyst may include a small amount of one or more cocatalysts such as Co, Zn, Mn, Mg, and Ni salts. One preferred cocatalyst is Ni. Another preferred cocatalyst is Zn. Another preferred cocatalyst is Mg. A description of the Cr-based catalyst with high specific surface area features in document WO 2009/158321, on pages 4 and 6.

The method according to the invention is preferably implemented continuously, this being highly advantageous from an industrial standpoint.

Generally speaking, the molar ratio of HF used relative to the organic compounds (hydrocarbons and halogen derivatives) is from 4:1 to 100:1 and preferably from 5:1 to 50:1. The use of superstochiometric ratios for the fluorination reaction is taught, for example, in WO 2008/054781 and WO 2008/040969.

The reaction may be implemented at a pressure of from 0.1 to 10 bar abs, and preferably from 0.3 to 8 bar abs.

The reaction may be implemented at a temperature of from 100 to 500° C., preferably from 200 to 450° C. The temperature of the reactor bed may be essentially uniform or may vary along the stream, either increasing or decreasing.

The contact time (volume of catalyst divided by the total flow rate of the reactants and other compounds at the inlet, adjusted in accordance with the reaction pressure and temperature) is typically from 1 to 100 s, preferably from 5 to 50 s.

It is also possible to provide a supply of oxidizing compound, particularly oxygen or chlorine, preferably oxygen, in order to extend the lifetime of the catalyst. In the example illustrated, the fluorination reactor 6 is supplied with oxygen by an oxygen supply line 5.

The molar ratio of oxygen relative to the organic compounds is preferably from 0.005 to 2 and more preferably from 0.01 to 1.5. The oxygen may be introduced in virtually pure form or else in the form of air, or alternatively in the form of a nitrogen/oxygen mixture.

A polymerization inhibitor may also be used to extend the lifetime of the catalyst, typically at a concentration of from 50 to 1000 ppm, more preferably from 100 to 500 ppm. It may be selected in particular from p-methoxyphenol, t-amylphenol, limonene, d,1-limonene, quinones, hydroquinones, epoxides, amines, and mixtures thereof. Preference is given to p-methoxyphenol and t-amylphenol. The co-supplying of polymerization inhibitor (not shown in the drawings) may make it possible to control the polymerization of the chloroolefins and thereby in particular to extend the lifetime of the catalyst described in document U.S. Pat. No. 5,714,651, incorporated here by reference.

Processing of the Stream Obtained from the Fluorination Reaction

The stream obtained from the reaction is recovered in a line 7 for reaction gases which is connected at the outlet of the fluorination reactor 6. This stream is cooled, and partly condensed, by cooling and partial condensation means 8 (such as exchangers and economizers) which are supplied by the line 7 for reaction gases.

The temperature of the stream after cooling and partial condensation is from −50 to 100° C., preferably from −40 to 80° C. The temperature selected is dependent on the pressure used (from vacuum to approximately 8 bar abs).

A line 9 for transporting partially condensed stream is connected at the outlet of the cooling and partial condensation means 8. This line transports the stream obtained from the reaction, after its cooling and its partial condensation.

The line 9 for transporting partially condensed stream supplies a separating flask 10, which allows the partially condensed stream to be separated into a gaseous fraction and a liquid fraction. The separating flask 10 is a horizontal or vertical reservoir capable of physically separating gases from liquids, preferably without input of energy.

The liquid fraction is recovered at the bottom of the separating flask 10 and is collected by a line 18 for withdrawing liquid fraction.

The gaseous fraction is recovered at the top of the separating flask 10 and is collected by a line 11, 13 for withdrawing gaseous fraction.

The gaseous fraction preferably represents from 25% to 60% of the stream, and the liquid phase preferably represents from 40% to 75% of the stream, in proportions by mass.

Heating means 12 are provided on the line 11, 13 for withdrawing gaseous fraction, in order to reheat the gaseous fraction and so to prevent any condensation during the subsequent compression.

The line 11, 13 for withdrawing gaseous fraction supplies a compressor 14. The compressor is manufactured from corrosion-resistant materials, such as 316L stainless steel, Hastelloy®, or Inconel®.

At the outlet of the compressor 14, the pressure is preferably from 5 to 40 bar abs, and more preferably from 7 to 25 bar abs.

The compressed gaseous fraction is collected by a line for supplying compressed gaseous fraction 15, 17, which is connected at the outlet of the compressor 14. Cooling means 16 may be provided on the line for supplying compressed gaseous fraction 15, 17, with the aim of cooling and possibly partially condensing the compressed gaseous fraction before the separating and purifying steps.

The compressed gaseous fraction is preferably cooled in this way to a temperature of from −10 to 50° C.

The line for withdrawing liquid fraction 18 opens into a pump 19. This pump 19 allows the liquid fraction to be conveyed to the separating and purifying means, by a line 20 for supplying compressed liquid fraction.

The means for separating and purifying the stream obtained from the reaction primarily comprise distillation means.

The distillation means are preferably operated at a pressure of from 5 to 40 bar abs, and more preferably from 7 to 25 bar abs.

In the embodiment illustrated, the distillation means comprise a first distillation column 21 and a second distillation column 23.

Each distillation column is provided with a bottom reboiler and with a system for condensing and reflux at the top, in a manner known per se.

The first distillation column 21 is supplied by the stream obtained from the reaction. The compressed liquid fraction (fed by the line 20 for supplying compressed liquid fraction) and the compressed gaseous fraction (fed by the line 15, 17 for supplying compressed gaseous fraction) supply the first distillation column 21 preferably at different levels, particularly according to their respective compositions.

The function of the first distillation column 21 is to separate the HCl and the HFO-1234yf, on the one hand, and the HF and organic compounds (chlorinated and/or fluorinated) on the other.

Accordingly, a line 22 for withdrawing intermediate stream is connected at the top of the first distillation column 21, and a line 1 for withdrawing unreacted hydrogen fluoride is connected at the bottom of the first distillation column 21.

The intermediate stream transported in the line 22 for withdrawing intermediate stream contains primarily HCl, HFO-1234yf, and also light compounds, namely nitrogen, oxygen, carbon monoxide, carbon dioxide, and other oxygen-containing derivatives. It may also contain HFC-245cb, obtained from the fluorination reaction, which may be subsequently recycled to the fluorination reactor, and also a small amount of HF, associated with the existence of azeotropes.

The stream referred to here as "stream of unreacted hydrogen fluoride", which is transported in the line 1 for withdrawing unreacted hydrogen fluoride, contains not only HF but also other, chlorinated and/or fluorinated organic compounds, such as HCFO-1233xf and HFC-245cb, which are reaction intermediates or organic compounds obtained from secondary reactions.

This stream of unreacted hydrogen fluoride is recycled to the fluorination reactor 6. Heating means 3 (such as exchangers and economizers) are provided on the line 1 for withdrawing unreacted hydrogen fluoride, in order to reheat and vaporize the stream before its entry into the fluorination reactor 6.

The line 4 for supplying hydrohalocarbon, the line 2 for supplying HF and/or the line 5 for supplying oxygen may be connected, for example, to the line 1 for withdrawing unreacted hydrogen fluoride, upstream and/or downstream of the heating means 3, so that the fluorination reactor 6 is supplied by a single conduit. Alternatively, the fluorination reactor 6 may be supplied by the respective lines at different locations. It is also possible to provide a line for direct recycling from the outlet of the fluorination reactor 6 to its inlet (or to one of its inlets), with appropriate means such as heating means, cooling means and/or compression means.

An energy coupling system may be provided between the heating means 3 and the cooling and partial condensation means 8, so that the calorific energy recovered in the course of the cooling and partial condensation of the gaseous stream obtained from the reaction are reused for the heating and vaporization of the stream at the inlet of the fluorination reactor 6.

The intermediate stream is subjected to separation in the second distillation column 23, in order to recover, on the one hand, the HFO-1234yf product of interest, and on the other hand the HCl with the light compounds. For this purpose, the second distillation column 23 is supplied at the inlet by the line 22 for withdrawing intermediate stream. At the outlet of this second distillation column 23, a line 24 for withdrawing hydrochloric acid is connected at the top and a line 25 for withdrawing 2,3,3,3-tetrafluoropropene is connected at the bottom.

The HFO-1234yf stream recovered at the bottom may contain HFC-245cb, and also a small amount of HF.

The HCl stream recovered at the top generally also contains the light compounds $O_2$, $N_2$, $CO_2$, and CO (and/or other oxygen-containing derivatives).

Further steps of purifying the HFO-1234yf stream may be employed, if necessary, on the basis, for example, of washing, extraction, decanting, distillation, or a combination of these operations.

The HF and the chlorinated or fluorinated organic compounds other than HFO-1234yf which are recovered during these further steps are preferably recycled to the fluorination reactor 6 (not shown).

Figure 2:
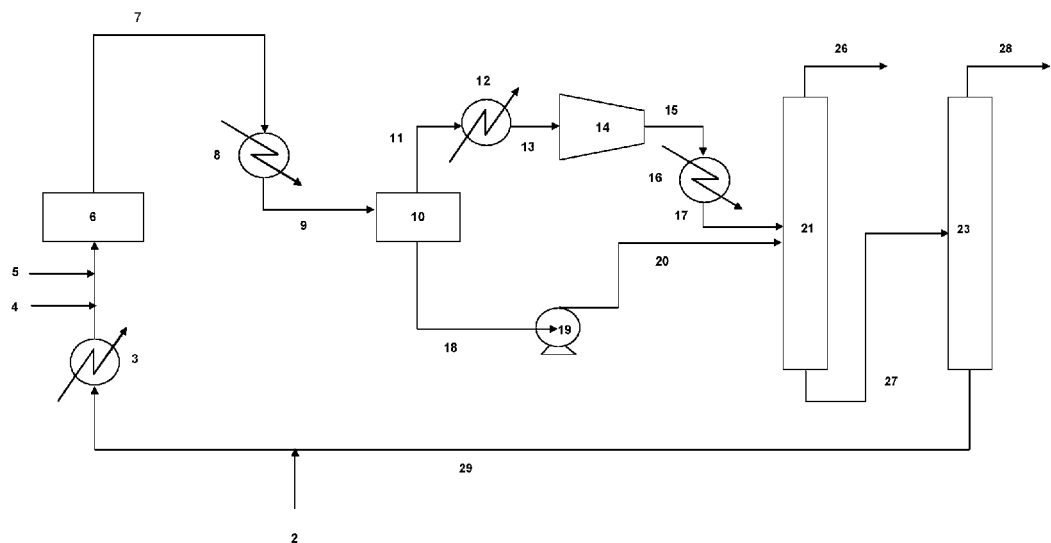
FIG. 2 represents schematically a plant in accordance with a second embodiment of the invention.

A second embodiment of the processing of the stream obtained from the reaction is illustrated in FIG. 2. According to this variant, the function of the first distillation column 21 is to separate the HCl on the one hand, and the HFO-1234yf, the HF, and the organic compounds (chlorinated and/or fluorinated) on the other.

Accordingly, a line 27 for withdrawing intermediate stream is connected at the bottom of the first distillation column 21, and a line 26 for withdrawing hydrochloric acid is connected at the top of the first distillation column 21.

The HCl stream recovered at the top generally also contains the light compounds $O_2$, $N_2$, $CO_2$ and CO (and/or other oxygen-containing derivatives).

The intermediate stream transported in the line 27 for withdrawing intermediate stream contains primarily HFO-1234yf, HF, and also other chlorinated and/or fluorinated organic compounds, such as HFC-245cb or HCFO-1233xf.

The intermediate stream is subjected to separation in the second distillation column 23, in order to recover, on the one hand, the HFO-1234yf product of interest, and on the other hand the other chlorinated and/or fluorinated organic compounds. For this purpose, the second distillation column 23 is supplied at the inlet by the line 27 for withdrawing intermediate stream. At the outlet of this second distillation column 23, a line 28 for withdrawing 2,3,3,3-tetrafluoropropene is connected at the top, and a line 29 for withdrawing stream of unreacted hydrogen fluoride is connected at the bottom.

The HFO-1234yf stream recovered at the top may contain HFC-245cb, and also a small amount of HF.

The stream of unreacted hydrogen fluoride, transported in the line 29 for withdrawing unreacted hydrogen fluoride, contains not only HF, but also other chlorinated and/or fluorinated organic compounds, such as HCFO-1233xf and HFC-245cb, which are intermediates in the fluorination reaction, or organic compounds obtained from secondary reactions (just as for the first embodiment). The stream is recycled to the fluorination reactor 6 in the same way as for the first embodiment.

Among numerous possible variants of the invention, particular mention may be made of the possibility of replacing the single items of equipment by a plurality of items of equipment operating in parallel or in series: for example, a number of fluorination reactors, and/or a number of first distillation columns, and/or a number of second distillation columns. The lines connecting the various items of equipment are adapted accordingly.

The invention claimed is:

1. A plant for producing 2,3,3,3-tetrafluoropropene, comprising:
    at least one fluorination reactor having an outlet, the reactor being supplied with halopropane and/or halopropene and hydrogen fluoride;
    a first line for reaction gases, which is connected at the outlet of the fluorination reactor;
    at least one cooling and partial condensation vessel having an outlet, the at least one cooling and partial condensation vessel being supplied by the first line for reaction gases;
    a second line for transporting a partially condensed stream, which is connected at the outlet of the cooling and partial condensation vessel;
    a separating flask having an outlet, the separating flask being supplied by the second line for transporting the partially condensed stream;
    a third line for withdrawing a gaseous fraction and a fourth line for withdrawing a liquid fraction, which lines are connected at the outlet of the separating flask;
    a compressor having an outlet, the compressor being supplied by the third line for withdrawing the gaseous fraction;
    a fifth line for supplying a compressed gaseous fraction, which is connected at the outlet of the compressor;
    a pump having an outlet, the pump being supplied by the fourth line for the withdrawn liquid fraction;
    a sixth line for supplying a compressed liquid fraction, which is connected at the outlet of the pump;
    at least one distillation vessel having an outlet, the distillation vessel being supplied by the fifth line for supplying the compressed gaseous fraction and by the sixth line for supplying the compressed liquid fraction; and
    a seventh line for withdrawing 2,3,3,3-tetrafluoropropene, an eighth line for withdrawing hydrochloric acid, and a ninth line for withdrawing unreacted hydrogen fluoride, wherein said lines are connected at the outlet of the at least one distillation vessel.

2. The plant as claimed in claim 1, wherein the ninth line for withdrawing unreacted hydrogen fluoride supplies the fluorination reactor.

3. The plant as claimed in claim 1, further comprising a heating device on the third line for withdrawing gaseous fraction.

4. The plant as claimed in claim 1, wherein the at least one distillation vessel comprise a first distillation column and a second distillation column, the fifth line for supplying the compressed gaseous fraction and the sixth line for supplying the compressed liquid fraction supplying the first distillation column.

5. The plant as claimed in claim 4, wherein:
the ninth line for withdrawing unreacted hydrogen fluoride is connected at the bottom of the first distillation column;
a tenth line for withdrawing an intermediate stream is connected at the top of the first distillation column, the tenth line supplying the second distillation column;
the eighth line for withdrawing hydrochloric acid is connected at the top of the second distillation column; and
the seventh line for withdrawing 2,3,3,3-tetrafluoropropene is connected at the bottom of the second distillation column.

6. The plant as claimed in claim 4, wherein:
the eighth line for withdrawing hydrochloric acid is connected at the top of the first distillation column;
a tenth line for withdrawing an intermediate stream is connected at the bottom of the first distillation column, the tenth line supplying the second distillation column;
the seventh line for withdrawing 2,3,3,3-tetrafluoropropene is connected at the top of the second distillation column; and
the ninth line for withdrawing unreacted hydrogen fluoride is connected at the bottom of the second distillation column.

7. The plant as claimed in claim 4, wherein the fifth line for supplying the compressed gaseous fraction and the sixth line for supplying the compressed liquid fraction supplies the first distillation column at different stages of said column.

8. The plant as claimed in claim 1, wherein the seventh line for withdrawing 2,3,3,3-tetrafluoropropene supplies further purification vessels.

* * * * *